(12) United States Patent
Ray

(10) Patent No.: US 6,283,984 B1
(45) Date of Patent: Sep. 4, 2001

(54) DURAL CLOSING SURGICAL FORCEPS

(75) Inventor: Charles D. Ray, Williamsburg, VA (US)

(73) Assignee: Tegementa, LLC, Williamsburg, VA (US)

( * ) Notice: Subject to any disclaimer, the term of this patent is extended or adjusted under 35 U.S.C. 154(b) by 0 days.

(21) Appl. No.: 09/435,914

(22) Filed: Nov. 8, 1999

Related U.S. Application Data

(63) Continuation of application No. PCT/US98/09087, filed on May 8, 1998.
(60) Provisional application No. 60/045,977, filed on May 8, 1997.

(51) Int. Cl.[7] .................................................. A61B 17/28
(52) U.S. Cl. ........................ 606/210; 606/205; 606/207
(58) Field of Search ................................ 606/205–208, 606/107, 210–211; 433/4; D24/143; D28/55

(56) References Cited

U.S. PATENT DOCUMENTS

| | | | |
|---|---|---|---|
| 2,214,984 | * | 9/1940 | Bachmann . |
| 3,209,753 | * | 10/1965 | Hawkins et al. ............... 606/207 |
| 4,822,277 | * | 4/1989 | Nevell ............................ 433/3 |
| 4,950,281 | * | 8/1990 | Kirsch et al. ................... 606/207 |
| 5,217,464 | * | 6/1993 | McDonald ..................... 606/107 |
| 5,520,704 | | 5/1996 | Castro et al. . |
| 5,565,004 | | 10/1996 | Christoudias . |
| 5,921,990 | * | 7/1999 | Webb ............................ 606/110 |

\* cited by examiner

*Primary Examiner*—David O. Reip

(57) ABSTRACT

The present disclosure is directed to a surgical forceps for joining tissue on opposed sides of an incision including a pair of extension members, wherein each extension member includes tissue engaging projections at a distal end thereof and are dimensioned and adapted to engage tissue on respective opposed sides of the incision. A central member is disposed between the extension members and defines a longitudinal axis. The central member includes a foot glide disposed at a distal end of the central member, wherein the foot glide defines a retaining surface dimensioned to retain tissue within the incision. The extension members are adapted for movement relative to the central member whereby movement of the extension members toward the central member causes the tissue engaging projections to engage and draw the tissue on the opposed sides of the incision toward each other in a general approximated relation. Also disclosed is a method of approximating tissue on opposed sides of an opening.

15 Claims, 2 Drawing Sheets

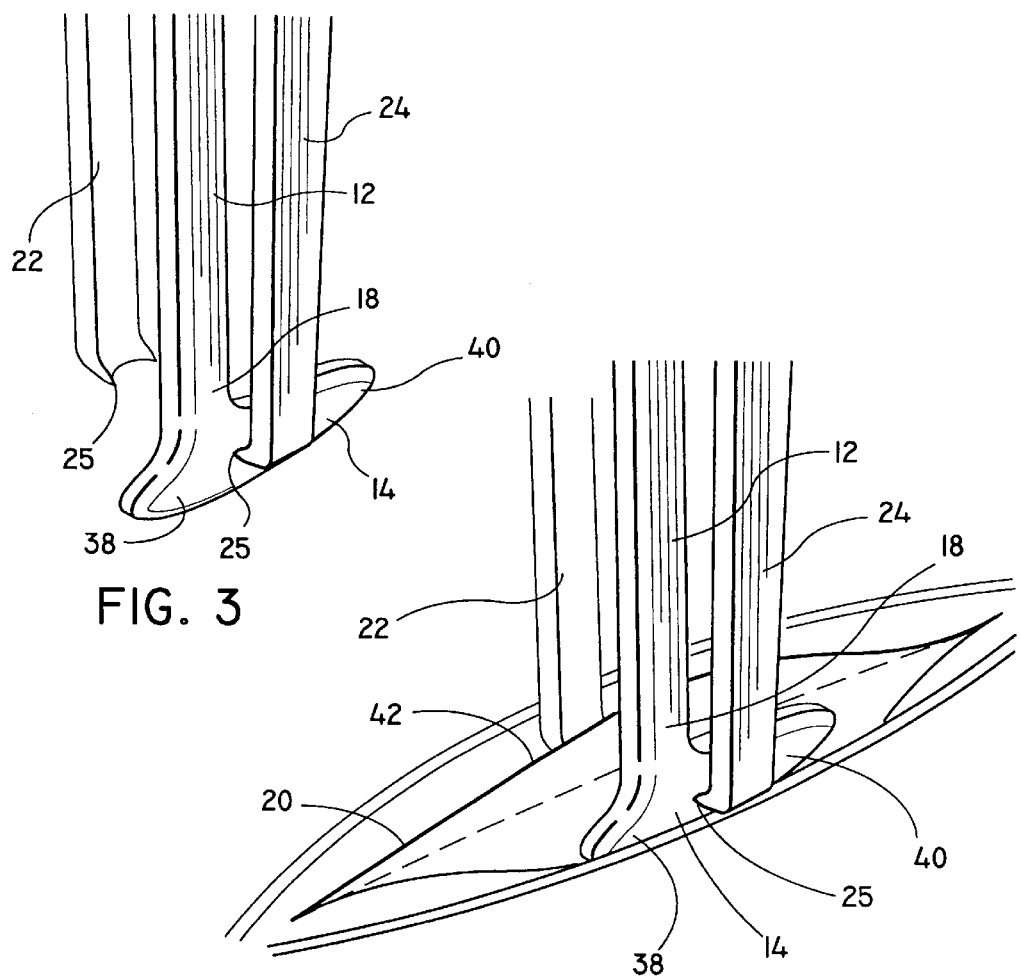
FIG. 3
FIG. 4
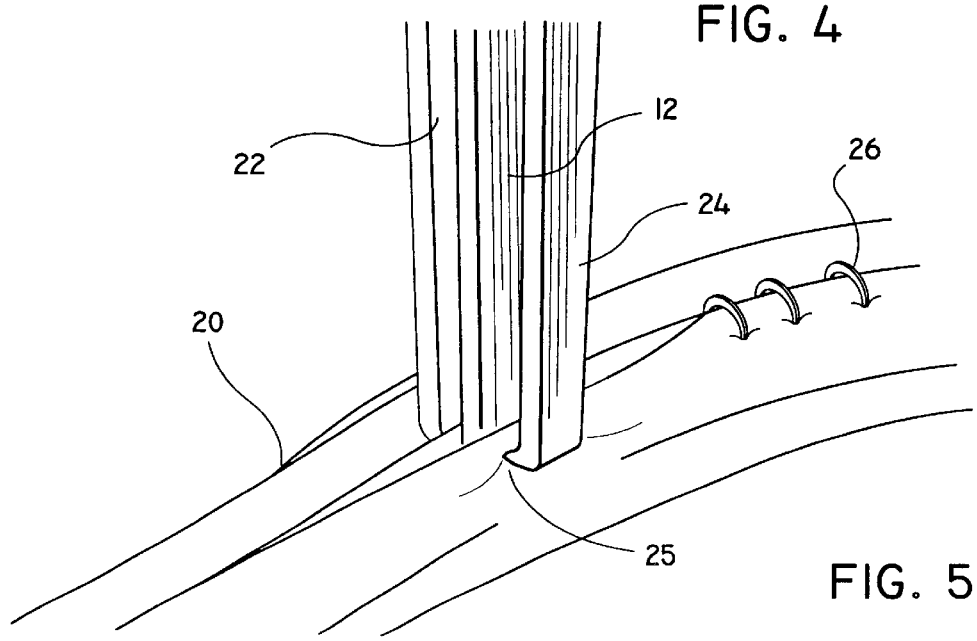
FIG. 5

DURAL CLOSING SURGICAL FORCEPS

CROSS-REFERENCE TO RELATED APPLICATIONS

This Patent Application is a continuation of PCT/US98/09087, filed May 8, 1998, which claims the benefit of U.S. Provisional Application No. 60/045,977 filed May 8, 1997.

BACKGROUND

1. Technical Field

The present disclosure concerns a device for drawing together opposite sides of an incised dura, and more particularly, to dural closing forceps for use in closing the dura after a durotomy.

2. Background of the Related Art

The dura is a tough protective membranous covering surrounding the central nervous system including the spinal cord and related nerve bundles. Surgery involving the dissection of the dura, a durotomy, is often required when operating on the brain or spine. A durotomy allows the surgeon to approach particular nerve structures for definitive dissection.

The central nervous system including the spinal cord and related nerve bundles are all constantly bathed in cerebrospinal fluid (CSF) all of which are encased by the dura. The CSF is constantly under pressure within the dura, this CSF pressure increases with certain disorders of the nervous system or by an erect posture of the head. The CSF is manufactured from circulating arterial blood passing through specialized filtration glands deep within brain cavities. The CSF then leaves the cavities and flows downward over the spinal structures by motion of the spine and pulsation of blood vessels. The CSF then flows back into the brain cavities where it is reabsorbed back into the body's circulatory system.

After the dura has been incised and the surgical procedure on the underlying nerve structures is performed, the dura must be closed to prevent any further escape of CSF. If the CSF leaks are not halted, the patient may have severe, persistent, disabling headaches. In some cases the durotomy may permit bacterial invasion resulting in life threatening meningitis. Water tight closure or sealing of durotomies is therefore an important aspect of neurosurgical practice.

Upon leakage of the CSF, nerve filaments or fragments of other, softer covering membranes are frequently flushed out and protrude beyond the margins of the durotomy. These filaments or fragments must be replaced and retained inside the dura as it is closed by the surgeon. Closing or sealing the dura after a durotomy requires retaining the filaments or fragments within the dura and holding the dural margins tightly together, aspirating the escaping fluid and obscuring blood while keeping the nerves and fragments from being caught into the closing seal and applying the sutures or clips. Optical magnification, often by a surgical microscope, is generally needed in order to complete the tedious procedure. It is quite clear that surgeons must possess considerable skill to effect a water tight closure of certain complex durotomies. Fortunately, once the dura is well closed, the margins are quickly sealed over with blood clots and-new tissue growth begins in a matter of hours permanently closing the durotomy in a matter of days.

Closing the dura can be quite difficult. It is usually performed using very small needles and sutures and specialized, fine-tipped grasping instruments. These instruments are necessary to hold together the incised or torn margins of the durotomy while the curved needle is passed through the two opposing dural margins or edges. The needle tracts or holes frequently create additional puncture sites through which CSF may leak or even squirt out. To make matters even more complex, the dura is protected by being surrounded with bony coverings such as the skull or the neural arches of the spine. Therefore, in order to operate on the brain or spine, bone material must be removed from the surgical site.

Closing the durotomy site also requires the removal of additional bone material, the extent of which relates generally to the space required to pass the curved needle through the incised dural margins. The margins which are torn or ragged result in excessive bleeding inside and around the dura thereby bringing blood into the surgical field and partially obscuring the durotomy surgical site.

A simplification of the durotomy closure procedure has been provided by United States Surgical Corporation (USSC) with small "C" shaped clips made from surgically implantable grade titanium. These clips are dispensed from a miniature surgical instrument called a clip applier also made by USSC. The clips do not perforate the dura but rather, hold the dural margins tightly together to halt the leak and promote dura regrowth. This instrument has been adapted from the larger clip appliers also made by USSC which are widely used in blood vessel surgery. The dural closure clips are generally available in sizes of 1.4 mm, 2 mm and 3 mm (outside diameters). Simple holding forceps are also provided by USSC to hold the durotomy margins together while the clips are being applied. An additional instrument is provided for opening and removing the clips.

Notwithstanding the ease of use of the dural clip applier and the holding forceps, suitable closure of the dural margins prior to applying the clips can still be a difficult task. The embodiments of the present disclosure solve these and other associated problems and provides a simple and easily applied instrument to draw together the dural margins while retaining the necessary nerve filaments and fragments inside the dura as it is closed by the surgeon.

SUMMARY

The present disclosure is directed to surgical forceps for use in closing a dural incision. The forceps include a pair of extension members cantilevered at a proximal end thereof and a central member disposed between the extension members, wherein the extension members and the central members are coupled together at the proximal end. The central member includes a foot glide transverse to a longitudinal axis thereof and positioned distally of the extension members, wherein the foot glide includes an intradural supporting surface for maintaining intradural tissue within a dura during a dural closing procedure. The foot glide further includes a rear portion and a front portion, wherein the front portion has a length greater than a length of the rear portion. The extension members include teeth for grasping tissue, wherein the teeth are disposed along a distal end of each extension member. The central member and each extension member includes a finger pad area. Each extension member is dimensioned and configured to move relative to the central member wherein movement of each extension member toward the central member results in a gripping force between the central member and each extension member at a distal end thereof.

Also disclosed is surgical forceps for joining tissue on opposed sides of an incision. The forceps include a pair of extension members, wherein each extension member includes tissue engaging projections at a distal end thereof and are dimensioned and adapted to engage tissue on respective opposed sides of the incision. A central member is disposed between the extension members and defines a longitudinal axis, wherein the extension members are coupled to the central member at the proximal end thereof. The central member includes a foot glide disposed at a distal end of the central member, wherein the foot glide defines a retaining surface dimensioned to retain tissue within the incision and is positioned distally of the extension members. The foot glide further includes a rear portion and a front portion, wherein the front portion has a length greater than a length of the rear portion. The extension members are adapted for movement relative to the central member whereby movement of the extension members toward the central member causes the tissue engaging projections to engage and draw the tissue on the opposed sides of the incision toward each other in a general approximated relation. The central member also includes opposed longitudinal support surfaces, wherein in the approximated relation of the tissue, the tissue is held between the tissue engaging projections of the extension members and the respective longitudinal support surfaces of the central member. The tissue securing projections further include at least one tooth projection for grasping tissue. The extension members and the central member each include a finger pad projection, the finger pad projection dimensioned to be engaged with a finger of the user.

Also disclosed is a method of approximating dural tissue on opposed sides of an opening in the dura. The method includes the step of providing a surgical forceps having a pair of extension members which include at least one tissue engaging projection at respective distal ends thereof and a central member disposed between the extension members and including a foot glide disposed at a distal end thereof. The method includes the step of positioning the surgical forceps with respect to the opening whereby the foot glide is disposed within the opening to retain tissue therewith and the tissue engaging projections are disposed on respective opposed sides of the opening. The method also includes moving each extension member toward the central member to cause the tissue engaging projections to draw the opposed sides of the dural tissue toward each other in approximated relation therewith and joining the opposed sides of the dural tissue to each other. The step of moving further includes drawing the opposed sides to the approximated relation whereby the sides are each held between the one tissue engaging projection of the respective extension members and the central member. The step of joining also includes applying a clip to the opposed sides of the tissue to securely fasten the approximated relation of the sides of tissue.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages may best be understood by reference to the following description, taken in connection with the accompanying drawings, in which:

FIG. 3 is a partial view illustrating a distal end of the surgical forceps of FIG. 1 in an open position;

FIG. 4 is a partial view illustrating a distal end of the surgical forceps of FIG. 1 with a central member inserted within a durotomy incision; and FIG. 5 is a partial view illustrating a distal end of the surgical forceps of FIG. 1 in a closed position.

DETAILED DESCRIPTION OF PREFERRED EMBODIMENTS

Figure 1:
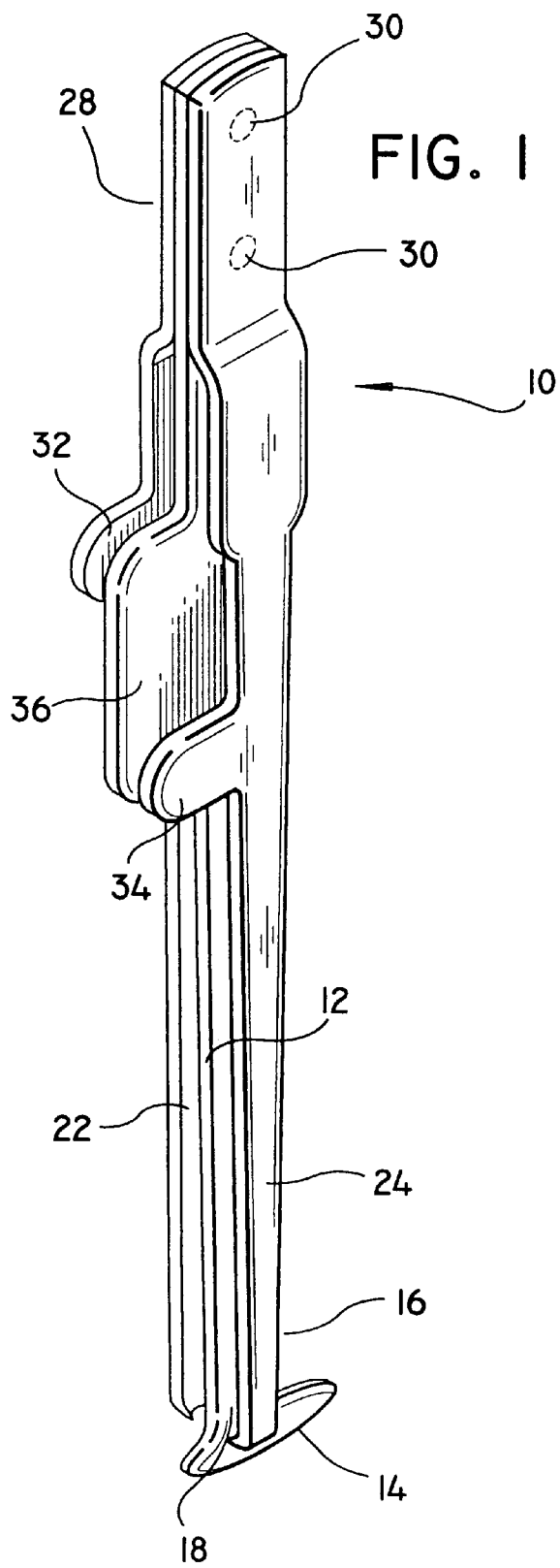
FIG. 1 is a view illustrating the dural closing surgical forceps according to the present disclosure.

The preferred embodiments of the apparatus and method disclosed herein are discussed in terms of dural closing surgical forceps and procedures for using the same. It is envisioned, however, that the disclosure is applicable to a wide variety of procedures including, but, not limited to both open and minimally invasive procedures including endoscopic and arthroscopic procedures wherein access to the surgical site is achieved through a cannula or small incision.

In the discussion which follows, the term "proximal", as is traditional, will refer to the portion of the structure which is closer to the operator, while the term "distal" will refer to the portion which is further from the operator.

The following discussion includes a description of the dural closing surgical forceps utilized in closing a dural incision followed by a description of the preferred method for using the dural closing forceps in accordance with the present disclosure.

Reference will now be made in detail to the preferred embodiments of the disclosure, which are illustrated in the accompanying figures. Turning now to the figures, wherein like components are designated by like reference numerals throughout the various figures, attention is first directed to FIGS. 1–4.

The dural closing forceps 10 include a central flat member 12 and a transversely positioned foot glide member 14 along a distal end 16 thereof. Each side of the central member 12 provides a surface 18 against which each of the incised or torn dural margins 20 can be held against. Opposite central member 12 are two slender extension members or blades 22 and 24 having distally located projections or teeth 25 to engage the incised dural margins or edges 20 and hold them tightly against surface 18 of central member 12.

Extension members 22 and 24 each include a projecting surface 32 and 34, respectively, which acts as a finger pad against which force, i.e. finger force from a surgeon, will be applied when operating the dural forceps 10 of the present disclosure. Similarly, central member 12 includes a projection surface 36 which is disposed between finger pads 32 and 34. The finger pads 32, 34 and 36 of the present disclosure may be of any suitable size and shape which will enable a surgeon to easily manipulate the dural forceps 10 and may also include a textured outside surface area to provide for better frictional adherence.

Figure 2:
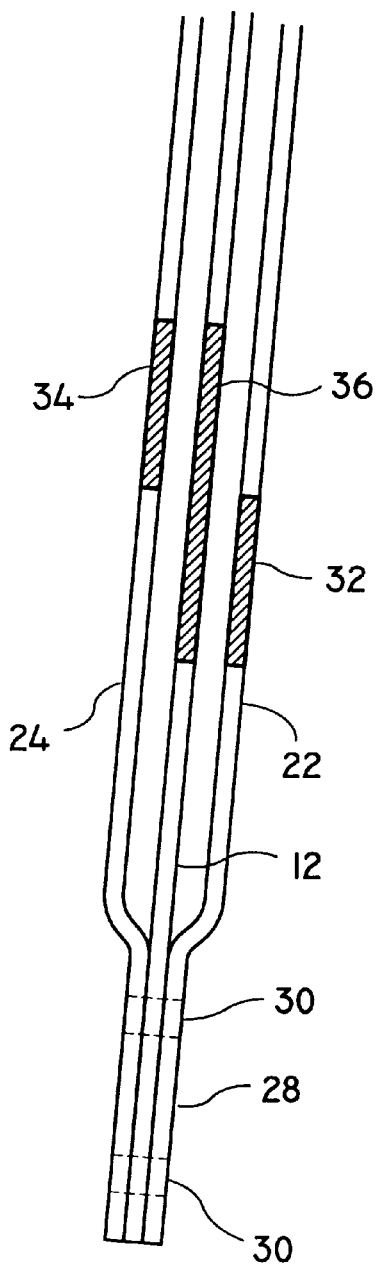
FIG. 2 is a partial cross-sectional view of the surgical forceps of FIG. 1.

As is shown in FIGS. 1 and 2, finger pads 32 and 34 are alternately spaced along opposing sides of finger pad 36. Finger pad 36 is preferably larger than finger pads 32 and 34 so as to provide an opposing surface for finger pads 32 and 34 when extension members 22 and 24 are manipulated to a closed position. In use the finger pads 32, 34 and 36 permit the surgeon's thumb to oppose either or both of the extension members 22 and 24 against central member 12. A surgeon's thumb and corresponding index finger (preferably of the left hand) may be placed on opposing surfaces of finger pads (32 and 36), (34 and 36) or (32 and 34) dependant on the particular manipulation of the members 12, 22 and 24 required. With the dural forceps being manipulated by one hand (left), a clip applier, as previously discussed, may be used to apply clips 26 to the re-approximated dural margins 20 with the other hand (right).

Central member 12 and both extension members 22 and 24 are firmly bonded together at the proximal end 28 by rivets 30 although other known bonding techniques such as welding are also contemplated. This bonding of the members 12, 22 and 24 maintain a cantilever relationship between all three components which allow the members 12, 22 and 24 to be rigid along the proximal end 28 but flexible along the distal end 16 of dural forceps 10.

With particular reference to FIG. 3, the distal end 16 of dural forceps 10 is shown in a relaxed or open position. Extension members 22 and 24 are preferably slightly shorter in length with respect to central member 12 although variations in the lengths of any member 12, 22 and 24 is obviously contemplated. Extension members 22 and 24 include projections or teeth 25 which are used to grasp tissue, i.e., dural margins 20, together before a clip 26 is applied. Central member 12 includes foot glide 14 which includes a smooth intradural tissue contacting surface (not shown). Foot glide member 14 glides against the underside of the re-approximated durotomy to act as a barrier, keeping the nerve filaments, membranous fragments and other intradural material from flushing or protruding out through the durotomy defect. The foot glide 14 is preferably transverse to the longitudinal axis of central member 12 and includes a rear portion 38 and a forward portion 40 generally separated by central member 12. The rear portion 38 of foot glide 14 is generally shorter in length than the forward portion 40. As is seen in FIGS. 4 and 5, a longer forward portion 40 ensures that the nerve filaments and membranous fragments are adequately covered by foot glide 14 prior to the application of clips 26.

With particular reference to FIG. 4, members 12, 22 and 24 are shown in an intermediate dural margins closing position. The foot glide 14 of central member 12 is shown holding the freely movable nerve filaments and fragments of membranes away from the dural margins 20. One edge 42 of the incised dural margins 20 is grasped by the toothed portion 25 (not shown) of extension member 22 and pinched against surface 18 of central member 12. Extension member 24 and corresponding toothed projection 25 is in a relaxed or open position.

As is shown in FIG. 5, the dural forceps 10 according to the present disclosure are in a fully closed position with extension member 24 holding one incised dural margin 20 against surface 18 of central member 12 and extension member 22 holding a second incised dural margin 20 likewise against opposing surface 18 of central member 12. In this closed position, the dural margins 20 are properly re-approximated without any of the nerve filaments, membranous fragments or intradural tissue protruding through the durotomy incision line. Once re-approximated, the dural margins 20 are held together with the application of clips 26 at small separated intervals, preferably in the range of 2–3 mm. After application of a clip 26, the three cantilevered components (central member 12 and extension members 22 and 24) are relaxed or opened to thereby release the grasp on the dural margins 20. The dural forceps 10 is subsequently moved further along the durotomy incision line permitting progressive clip 26 applications.

The dural closure forceps 10 according to the present disclosure is capable of holding in position the two incised dural margins or edges 20 while keeping nerve filaments and fragments of membranes from erupting out from the dural margins 20 as dural closure clips 26 or sutures are applied. Therefore, a surgeon with only one hand is capable of holding the dural margins 20 and the nerve filaments and fragments of membranes in the proper relationship for closing the dural margins 20 of the durotomy.

The operative steps involved with closure of an incised dura utilizing the dural forceps 10 of the present disclosure will now be discussed. The method described below will discuss a method of closing an incised dura post the performance of a standard durotomy procedure. The method will also be discussed with respect to a particular sequence, i.e., finger pads 32, 34 and 36 and corresponding hand and finger positions, although alternate opposite sequences are obviously contemplated.

Upon completion of a durotomy and upon commencing of the procedure involved in closing the incised dura, the dural forceps 10 according to the present disclosure are grasped by a surgeon in one hand with finger pad 32 and finger pad 36 being held against an index finger and corresponding thumb, respectively. Using an additional pair of simple forceps in an opposite hand, the surgeon brings one cut dural margin 20 into the space above the foot glide 14 and between the central member 12 and extension member 22. The principal thumb then forces finger pad 36 against finger pad 32 bringing the toothed projections 25 of extension member 22 and surface 18 of central member 12 together to thereby firmly grasp the one cut dural margin 20 of the durotomy. Similarly, the second cut dural margin 20 is then brought against opposite surface 18 of central member 12. The principal thumb is then slipped downward against finger pad 34 of extension member 24 to thereby pinch the second cut dural margin 20 against the surface 18 of central member 12. At this point, the nerve filaments and free membrane fragments are kept from flowing or protruding into the re-approximated dural margins 20 by the foot glide 14, as is shown in FIG. 5. Once the dural margins 20 are re-approximated, clips 26 are applied in the same manner as described earlier. After applying the clips 26, the clip applier remains in a closed position thereby providing a grasping force to the re-approximated dural margins 20 and serving as a temporary forceps while the dural forceps 10 are relaxed (opened) and moved a short distance, i.e., about 2 or 3 mm, along the durotomy margins 20 to commence the next re-approximation and clipping maneuver.

It will be understood that various modifications may be made to the embodiments disclosed herein. For example, the dural forceps 10 may be fabricated from either a surgical grade steel or other known surgical alloys. Also, the dural forceps 10 may be fabricated from a plastic resin making it both less expensive and readily disposable. Therefore, the above description should not be construed as limiting, but merely as exemplifications of preferred embodiments. Those skilled in the art will envision other modifications within the scope and spirit of the claims appended hereto.

What is claimed is:

1. A surgical forceps for use in closing a dural incision comprising:
   a pair of extension members cantilevered at a proximal end thereof; and
   a central member disposed between the extension members including a foot glide transverse to a longitudinal axis thereof, wherein the foot glide includes a front portion and a rear portion, and wherein the front portion has a length greater and a length of the rear portion.

2. The surgical forceps according to claim 1, wherein the extension members include at least one tooth for grasping tissue.

3. The surgical forceps according to claim 1, wherein the central member and each extension member includes a finger pad area.

4. The surgical forceps according to claim 2, wherein the at least one tooth are disposed along a distal end of each extension member.

5. The surgical forceps according to claim 1, wherein each extension member is dimensioned and configured to move relative to the central member wherein movement of each extension member toward the central member results in a gripping force between the central member and each extension member at a distal end thereof.

6. The surgical forceps according to claim 1, wherein the foot glide includes an intradural supporting surface for maintaining intradural tissue within a dura during a dural closing procedure.

7. The surgical forceps according to claim 1, wherein the extension members and the central members are coupled together at the proximal end.

8. The surgical forceps according to claim 1, wherein the foot glide is positioned distally of the extension members.

9. An apparatus for joining tissue on opposed sides of an incision, which comprises:

a pair of extension members, each extension member having at least one tissue engaging projections at a distal end thereof, the at least one tissue engaging projections being dimensioned and adapted to engage tissue on respective opposed sides of an incision;

a central member disposed between the extension members and defining a longitudinal axis, the central member having a foot glide disposed at a distal end of the central member, the foot guide defining a retaining surface comprising a front portion and a rear portion, wherein the front portion has a length greater than a length of the rear portion, the foot glide being dimensioned to retain tissue within the incision; and the extension members being adapted for movement relative to the central member whereby movement of the extension members towards the central member causes the at least one tissue engaging projections to engage and draw the tissue on the opposed sides of the incision toward each other in general approximated relation.

10. The apparatus according to claim 9, wherein the central member includes opposed longitudinal support surfaces, wherein in the approximated relation of the tissue, the tissue is held between the at least one tissue engaging projections of the extension members and the respective longitudinal support surfaces of the central member.

11. The apparatus according to claim 10, wherein the at least one tissue engaging projections are disposed along a distal end of each extension member.

12. The apparatus according to claim 11, wherein the at least one tissue engaging projection comprises at least one tooth for grasping tissue.

13. The surgical forceps according to claim 10, wherein the extension members are coupled to the central member at the proximal end thereof.

14. The apparatus according to claim 9, wherein the extension members and the central member each include a finger pad projection, the finger pad projection dimensioned to be engaged with a finger of the user.

15. The apparatus according to claim 9, wherein the foot glide is positioned distally of the extension members.

* * * * *